United States Patent [19]

Derbyshire

[11] Patent Number: 5,211,652
[45] Date of Patent: May 18, 1993

[54] SCALPEL

[76] Inventor: Bruce Derbyshire, P.O. Box 526, Adamsville, R.I. 02801

[21] Appl. No.: 771,136

[22] Filed: Oct. 3, 1991

[51] Int. Cl.⁵ .............................................. A61F 5/14
[52] U.S. Cl. ................................... 606/182; 606/206
[58] Field of Search ............... 606/182, 181, 167, 171, 606/172, 185, 205, 206

[56] References Cited

U.S. PATENT DOCUMENTS 4,760,848 8/1988 Hasson .................................. 606/206

Primary Examiner—Edgar S. Burr
Assistant Examiner—Anthony H. Nguyen
Attorney, Agent, or Firm—Samuels, Gauthier & Stevens

[57] ABSTRACT

A retractable blade scalpel comprises a knife blade, a flexible envelope, and an elongated housing forming a blade containment area. When pressure is applied to the flexible envelope the knife blade is longitudinally displaced to a protruding usage position. The knife blade remains outside the housing as long as pressure is applied to the flexible envelope.

8 Claims, 2 Drawing Sheets

SCALPEL

BACKGROUND OF THE INVENTION

The present invention relates to a retractable blade safety device, in particular a scalpel, for surgical uses.

Due to the dangers posed to medical personnel who treat individuals with certain transmittable diseases, such as the AIDS virus, it is necessary that doctors and other medical personnel wear surgical gloves in the course of performing the respective professional activities. Surgeons are in particularly high risk positions due to the unavoidable exposure to patient blood.

Prior art retractable blade safety devices help to alleviate some of the risk to medical personnel in handling surgical knifes. Prior art actuators for retractable blade safety devices include sliding actuator buttons (U.S. Pat. No. 4,320,576), sliding thumb pieces (U.S. Pat. No. 4,233,734), pencil or ballpoint pen-type actuators (U.S. Pat. Nos. 4,337,576 and 4,663,846), rotating barrels (U.S. Pat. No. 4,730,613), moving shells or shrouds (U.S. Pat. Nos. 4,393,587 and 4,414,974), and mechanisms which convert a radial force into an axial force (U.S. Pat. No. 4,757,612).

However, such prior art devices present an additional difficulty to surgeons in that they are difficult to manipulate while wearing surgical gloves. Moreover, prior art actuators, particularly slidable thumb switches and pen type actuators, pose the further risk that they may cause puncturing or tearing of surgical gloves during use.

It is therefore an object of the present invention to provide a retractable blade scalpel, or other like cutting device, which utilizes as an actuator a flexible envelope which when compressed, causes a knife blade to protrude from within a safe housing.

A companion object of the present invention is the provision of a retractable blade scalpel which can be readily manipulated by surgeons without the risk of damaging surgical gloves and other like protective clothing.

SUMMARY OF THE INVENTION

To this end, the invention comprises a knife blade, a flexible envelope, and an elongated housing forming a blade containment area.

The elongated housing serves as a knife handle and contains the flexible envelope which is exposed through one or more openings in the housing. The flexible envelope and the openings are positioned such that at least one finger and/or thumb tip of the user will come in contact with the flexible envelope when the knife handle is grasped. When pressure is applied to the flexible envelope, the knife blade is longitudinally displaced from within the elongated housing to protrude exteriorly of the housing for usage.

Pressure applied to the flexible envelope causes the envelope to become deformed in such a way that the knife blade is forced out of the blade containment area of the elongated housing. The knife blade remains outside the housing as long as pressure is applied to the flexible envelope.

BRIEF DESCRIPTION OF THE DRAWINGS

A more detailed description of the invention will now be presented with reference to the accompanying drawings in which.

DETAILED DESCRIPTION

Figure 1:
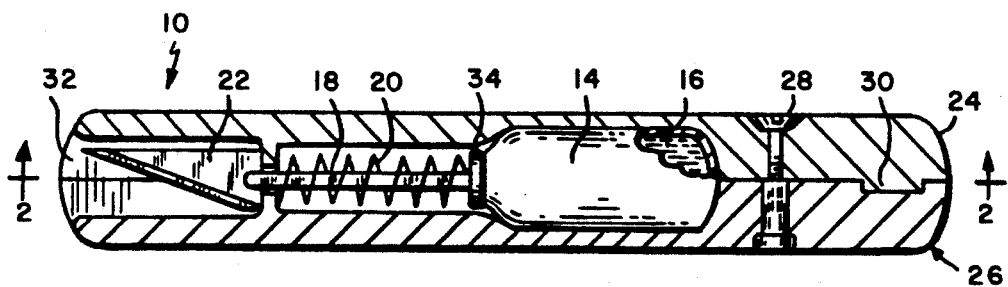
FIG. 1 is a longitudinal sectional view of a scalpel in accordance with the present invention.

FIGS. 1–4 show a retractable blade scalpel 10 of the present invention including an elongated housing 12, a flexible envelope 14 containing a fluid 16, a piston 18, a spring 20, and a knife blade 22. Housing 12 serves as a handle and includes top and bottom housing portions 24 and 26 joined by any convenient means such as for example, a screw 28 and dovetail 30. Housing 12 forms a blade containment area 32 containing the blade 22, and an envelope containment area 34 containing the envelope 14, piston 18, and spring 20. Fluid 16 is a sterile liquid in the preferred embodiment.

Figure 2:
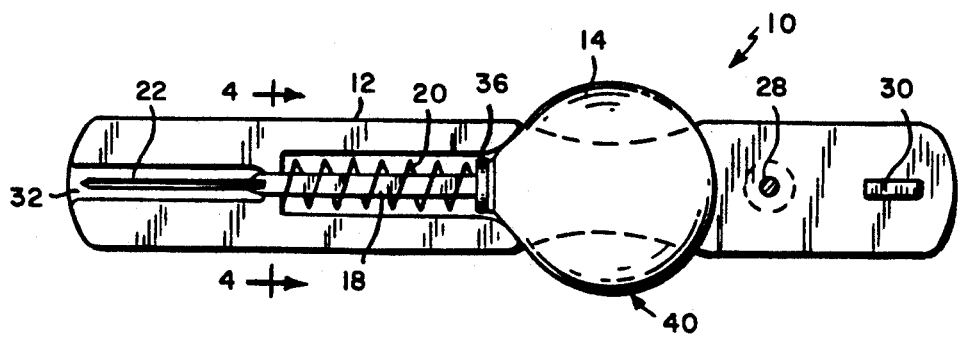
FIG. 2 is another longitudinal sectional view taken on line 2—2 of FIG. 1.

A head 36 of the piston 18 abuts the envelope 14, and the opposite end 38 of the piston 18 is attached to the blade 22. As shown in FIGS. 1–2, when the scalpel 10 is not in use, the spring 20 forces the piston 18 away from the blade containment area 32. Blade 22 is thus safely retracted into and contained within area 32, and the head 36 thus forcibly abuts the envelope 14.

Figure 3:
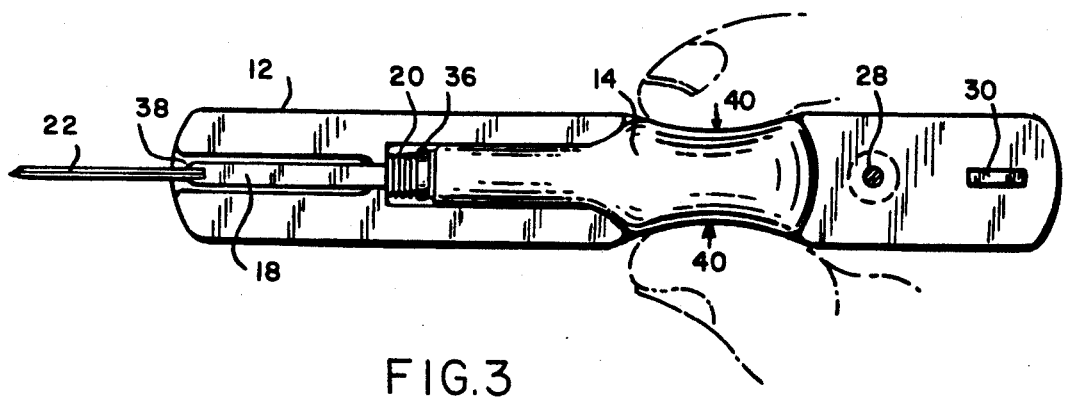
FIG. 3 is a view similar to FIG. 2 illustrating the scalpel in use with the knife blade extended.
Figure 4:
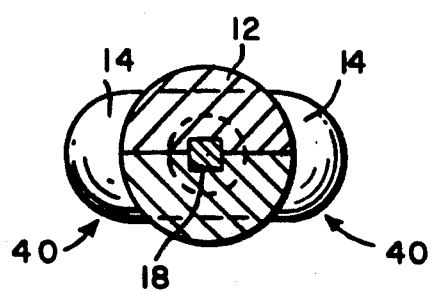
FIG. 4 is a cross-sectional view taken along line 4—4 of FIG. 2.

FIG. 3 shows the envelope 14 confined within area 34 such that when a compression force is applied to the actuator surfaces 40, the envelope 14 deformably overcomes the force of the spring 20 and forces the piston 18, and hence the blade 22, to become longitudinally displaced. Blade 22 is thereby displaced to a protruding position exterior of the housing 12. As shown in FIG. 4, when the scalpel 10 is not in use, the actuator surfaces 40 extend sufficiently laterally beyond the housing 12 such that the blade 22 is easily displaced to its fully extended position by the user applying a comfortable pressure to the actuator surfaces 40.

Figure 5:
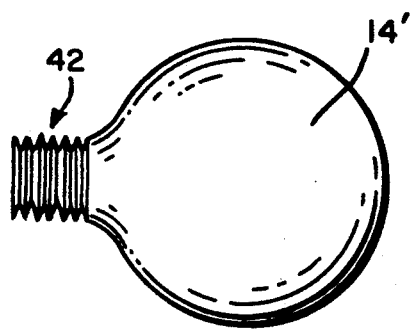
FIG. 5 is an illustration of an alternative design of the flexible envelope.
Figure 6:
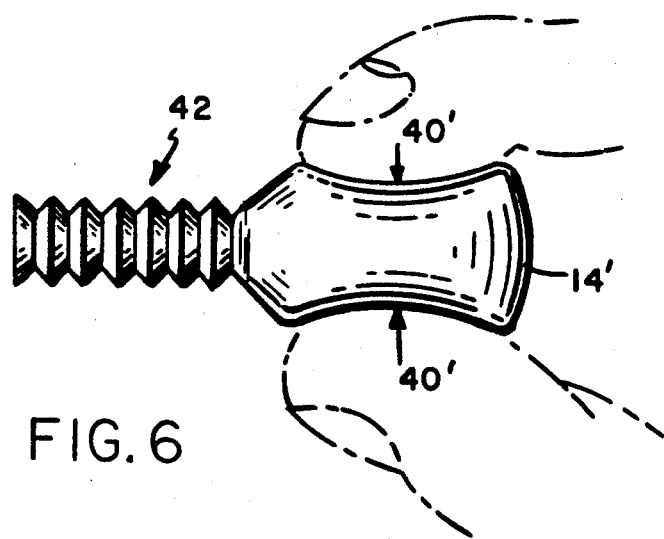
FIG. 6 is a view similar to FIG. 5 illustrating the flexible envelope in a deformed condition.

FIGS. 5–6 illustrate an alternative design of the flexible envelope designated 14' which has a bellow-like nose 42 having a pleated structure more readily expandable into engagement with the head 36 of the piston 18 when pressure is applied to actuator surfaces 40'.

I claim:

1. A retractable blade cutting device comprising;
   an elongated housing forming a blade containment area and an envelope containment area;
   a blade reciprocally movable between a withdrawn position within said blade containment area and an extended position protruding exteriorly of said housing;
   biasing means for exerting a biasing force urging said blade into said withdrawn position;
   a flexible closed envelope partially enclosed within said envelope containment area, said envelope containing a fluid and having at least one actuator surface accessible from the exterior of said housing; and
   means to position said blade in the extended position only upon application and maintenance of pressure to said envelope, said means including a piston associated with said blade and engageable by said flexible envelope such that when pressure is applied to said actuator surface, said piston is actuated by said envelope, thereby overcoming the force exerted by said biasing means and causing said blade to shift from said withdrawn position to said extended position, and upon release of said pressure said biasing means returning said blade to said withdrawn position.

2. A device as claimed in claim 1, wherein said fluid within said flexible envelope is a liquid.

3. A device as claimed in claim 1, wherein said flexible envelope includes a pleated portion which extends when pressure is applied to said actuator surface.

4. A retractable blade cutting device comprising:
an elongated housing forming a handle and internally defining a blade containment area;
a blade assembly including a blade mounted for reciprocal movement between a retracted position containing within said blade containment area, and an extended position protruding from said blade containment area exteriorly of said housing;
biasing means for exerting a biasing force urging said blade into said blade containment area; and
a flexible closed envelope containing a fluid and arranged within said housing adjacent to said blade assembly, said envelope having an actuator surface accessible from the exterior of said housing, and means to position said blade in the extended position only upon application and maintenance of pressure to said envelope to overcome the force exerted by said biasing means and urge said blade into said extended position, release of said pressure resulting in said biasing means returning said blade to said blade containment area.

5. A device as claimed in claim 4, wherein said fluid within said flexible envelope is a liquid.

6. A device as claimed in claim 4, wherein said flexible envelope includes a pleated portion which extends when pressure is applied to said actuator surface.

7. A device as claimed in claim 1, wherein said biasing means further includes resilient means for returning said blade to said blade containment area when said pressure is relieved.

8. A device as claimed in claim 4, wherein said biasing means further comprises a resilient means for returning said blade to said retracted position when said pressure is relieved.

* * * * *